US008092452B2

(12) United States Patent
Stamps et al.

(10) Patent No.: US 8,092,452 B2
(45) Date of Patent: Jan. 10, 2012

(54) PERCUTANEOUS DELIVERY SYSTEM FOR TREATMENT OF OSTEONECROSIS OF THE HIP AND METHODS OF USE THEREOF

(75) Inventors: Stephen D. Stamps, Memphis, TN (US);
Scott D. Boden, Atlanta, GA (US);
James S. Marotta, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 417 days.

(21) Appl. No.: 11/751,321

(22) Filed: May 21, 2007

(65) Prior Publication Data
US 2008/0294085 A1 Nov. 27, 2008

(51) Int. Cl.
*A61B 17/56* (2006.01)

(52) U.S. Cl. .... 606/60; 604/522; 604/890.1; 623/23.51; 424/423

(58) Field of Classification Search .................... 604/11, 604/15, 57, 93.01, 285, 286, 522, 890.1; 623/17.11, 17.16, 23.52, 23.51, 23.63, 919; 424/423, 426, 424, 425; 606/60, 62, 65, 606/309–318
See application file for complete search history.

(56) References Cited

U.S. PATENT DOCUMENTS

| 6,827,720 | B2 * | 12/2004 | Leali .............................. 606/96 |
| 7,198,047 | B2 | 4/2007 | Lambrecht et al. |
| 2003/0009235 | A1 | 1/2003 | Manrique et al. |
| 2004/0064193 | A1 | 4/2004 | Evans et al. |
| 2005/0152949 | A1 * | 7/2005 | Hotchkiss et al. ............ 424/423 |
| 2006/0002980 | A1 * | 1/2006 | Ringeisen et al. ............ 424/426 |
| 2007/0088436 | A1 | 4/2007 | Parsons et al. |
| 2008/0249627 | A1 * | 10/2008 | Moehlenbruck et al. .. 623/17.16 |

* cited by examiner

*Primary Examiner* — Kevin C Sirmons
*Assistant Examiner* — Kami A Bosworth

(57) ABSTRACT

Systems, methods, and carriers for percutaneous delivery of growth factors to treat osteonecrosis in the hip and other locations are disclosed. A rolled carrier comprising a biphasic ceramic rolled by a collagen sponge, and carrying a growth factor, are inserted via a delivery tube or cannula into a preformed hole in bone without overstuffing of the carrier or growth factor.

7 Claims, 9 Drawing Sheets

PERCUTANEOUS DELIVERY SYSTEM FOR TREATMENT OF OSTEONECROSIS OF THE HIP AND METHODS OF USE THEREOF

FIELD OF THE INVENTION

The present invention relates to treatment of osteonecrosis. More particularly, the invention relates to a system for delivering a growth factor and its carrier so as to prevent over-concentrating, overstuffing or overpacking of the growth factor and/or its carrier.

BACKGROUND

Fractures of the proximal femur are devastating events for individuals, particularly for the elderly for whom these types of injuries are relatively frequent. In the United States alone there are more than 300,000 hip fractures (Hudson et al., Clin. Orthop., pp. 59-66, 1998), and by the year 2050 the number is expected to double (Koval and Zuckerman, J. Am. Acad. Orthop. Surg., 2(3): 141-149, 1994; Montgomery and Lawson, Clin. Orthop., pp. 62-68, 1978).

Osteonecrosis of the hip, also known as avascular necrosis (AVN), aseptic necrosis, ischemic bone necrosis, or osteochondritis dissecans, is a condition where the blood supply to the femoral head is compromised, resulting in degeneration and collapse of the hip. AVN most commonly occurs in individuals between the ages of 30 and 60. Although it can occur in any bone, AVN most commonly affects the ends of long bones or the epiphysis, such as the femur. Other common sites are the humerus, knees, shoulders, and ankles. The disease can affect one or more bones at the same time or at different times. AVN can also be involved in other bone diseases, such as osteoarthritis.

A system and method of treating osteonecrosis is described in U.S. Pat. No. 6,827,720 (the '720 Patent). The '720 Patent describes a technique of drilling channels in bone (which is termed core decompression) and inserting growth factors followed by a plug (not containing growth factors), which compresses the growth factors. The channel is sealed with a plug or screw that is advanced into each channel and compacts the bone-growth-inducing compound. The bone-growth compound is therefore biased toward the distal end of the channel. The compacting event forces the compound into the necrotic section of bone, and the pressure causes the distal bone voids to be filled with bone-growth material. The plug or screw reinforces the subchondral bone and adds structural strength to the necrotic bone, preventing collapse of the bone.

Core decompression treatment involving drilling a hole into the femoral head and packing autograft or allograft bone is intended to stimulate the growth of blood vessels and new bone in the femoral head. Bone morphogenic protein (BMP) is known to stimulate both new bone and new blood vessel formation. Additionally, it is believed that the drilling procedure itself also stimulates bone formation by releasing indigenous growth factors within the surrounding bone. Overstuffing or overpacking of BMP on a collagen carrier, however, is associated with bone resorption prior to new bone formation because the overstuffing or overpacking results in too high of a concentration of BMP (see Burkus, et al., "Short-term effects of rhBMP-2/absorbable collagen sponge in a cancellous bone environment," *The Spine Journal* 6:73S-74S (2006)). Bone resorption could result in further collapse of the hip if an excessively high concentration of BMP were used in core decompression. Such excessively high concentrations can arise when a carrier having the correct concentration is overpacked in the hole. A method to deliver BMP and other growth factors on a carrier for a core decompression procedure without overpacking would therefore maximize the potential for success.

SUMMARY OF THE INVENTION

The need for delivery of one or more growth factors during core decompression without overstuffing or overpacking is fulfilled by providing, in a first aspect, a system for percutaneous delivery of a growth factor to a pre-drilled space in a bone of a patient, which includes: an applicator, the applicator having a hollow core extending along the length of the applicator, with proximal and distal ends, and a length such that when the distal end of the applicator is in contact with a pre-drilled space in a bone the proximal end is exposed; a carrier including one or more growth factors, the carrier being of a size capable of being inserted into the pre-drilled space through the core of the applicator; and a pusher device capable of advancing the carrier through the applicator and into the pre-drilled space without overstuffing the carrier. In certain embodiments, the applicator and pusher mechanically engage with each other to prevent over-extension of the pusher in the distal direction, and hence overpacking of the carrier into the pre-drilled space.

In one embodiment, the carrier includes a collagen sponge material, which may be rolled into a substantially cylindrical shape and may also be wrapped by a flexible, sterile sheet. The carrier may also include biphasic ceramic granules or any compression-resistant material, which may be placed on the collagen sponge material prior to being rolled into a substantially cylindrical shape. The compression-resistant material may be biodegradable or non-biodegradable. The granules or the compression-resistant material provide mechanical support to the sponge that make the sponge compression-resistant. The growth factor is applied to the collagen sponge material prior to rolling it into a substantially cylindrical shape. In another embodiment the carrier may be formed from any ceramic granules or any compression-resistant material. In this embodiment, the growth factor is applied to the ceramic granules or compression-resistant material.

In one embodiment the growth factor is in solution, which may be soaked into or applied onto the collagen sponge material. In another embodiment the growth factor solution may be soaked into or applied onto the biphasic ceramic granules or any compression resistant material.

In different, non-limiting embodiments of the invention, the growth factor may be a bone morphogenetic protein, recombinant versions thereof, fragments derived therefrom, and recombinant human versions thereof, such as BMP-2, rhBMP-2, BMP-4, rhBMP-4, BMP-6, rhBMP-6, BMP-7 (also known as OP-1), rhBMP-7, GDF-5, rhGDF-5, BMP-9, or rhBMP-9. Alternatively, the growth factor may be selected from the group consisting of platelet-derived growth factor (PDGF), transforming growth factor β (TGF-β), insulin-related growth factor-I (IGF-I), insulin-related growth factor-II (IGF-II), fibroblast growth factor (FGF), beta-2-microglobulin (BDGF II) (as disclosed in U.S. Pat. No. 6,630,153), PTH, PGE2-agonist, granulocyte colony stimulating factor (G-CSF), vascular endothelial growth factor (VEGF), matrix metalloproteinase (MMP), statins, recombinant versions thereof and recombinant human versions thereof. Recombinant versions of the growth factors may be useful, for example, for veterinary purposes.

In a second aspect, a system for delivery of a growth factor to a pre-drilled space in a bone of a patient is provided and includes: a threaded applicator, the threaded applicator having a hollow core, spaces along the side and/or at the bottom of the threaded applicator and a predetermined length, the predetermined length being such that the threaded applicator will fit into the pre-drilled space in the bone of the patient; and a carrier that includes one or more growth factors, the carrier sized for insertion into the core of the threaded applicator without overstuffing the carrier. The threaded applicator may be left within the patient in certain embodiments.

In one embodiment the carrier includes a collagen sponge material, which may be rolled into a substantially cylindrical shape and may also be wrapped by a flexible, sterile sheet. The flexible sheet assists with the administration of the carrier into the pre-drilled space, without over-stuffing the carrier. One can, optionally, remove the flexible sheet from the patient after delivery of the carrier. The carrier may also include biphasic ceramic granules or any compression-resistant material, which may be placed on the collagen sponge material prior to being rolled into a substantially cylindrical shape.

In one embodiment the growth factor is in solution, which may be soaked into or applied onto the collagen sponge material. In another embodiment the growth factor solution may be soaked into the biphasic ceramic granules or other compression-resistant material.

In a third aspect, a percutaneous method of delivering an effective amount of a growth factor to a pre-drilled space in a bone of a patient is provided and includes the steps of: (a) inserting a percutaneous applicator into or adjacent to a pre-drilled space in a bone of a patient, the percutaneous applicator having a hollow core extending the length of the percutaneous applicator, proximal and distal ends, and a length such that when the distal end of the percutaneous applicator is in contact with a pre-drilled space in a bone the proximal end is exposed; (b) inserting into the percutaneous applicator a carrier having one or more growth factors; and (c) pushing the carrier through the percutaneous applicator and into the pre-drilled space without overstuffing of the carrier. This percutaneous approach would be preferable to an open surgical approach which often results in significant muscle damage as the blunt surgical dissection tears through each layer of tissue until the femur is exposed. Using a percutaneous applicator which passes through a small incision in the skin is also known as a 'minimally invasive' approach. Patients treated with a percutaneous approach often have less post-operative pain and are discharged from the hospital sooner than those treated with an open approach.

In a fourth aspect, a method of delivering an effective amount of a growth factor to a pre-drilled space in a bone of a patient is provided that includes the steps of: (a) providing a threaded applicator, the threaded applicator having a hollow core, spaces, slots, or holes along its side and/or its bottom, and a predetermined length, the predetermined length sized to fit into a pre-drilled space in a bone of a patient; (b) inserting into the threaded applicator a carrier having one or more growth factors; and (c) inserting the threaded applicator into the pre-drilled space. The threaded applicator may preferably be placed into the patient through a percutaneous approach, but other approaches are contemplated.

In a fifth aspect, a carrier for insertion into a pre-drilled hole in a bone of a patient is provided that includes: a flexible, sterile sheet; a collagen sponge placed on one face of the flexible, sterile sheet, the collagen sponge having a growth factor; wherein the flexible, sterile sheet is rolled into a cylindrical shape after the placement of the collagen sponge on the flexible, sterile sheet, the flexible, sterile sheet being on the outside of the cylindrical shape; and wherein the cylindrical shape is of a length such that it may be inserted into the pre-drilled hole without being overstuffed or overpacked. In some embodiments the sterile sheet may be removed from the implant after insertion of the implant into the pre-drilled hole. In other embodiments the collagen sponge is wrapped around a compression-resistant material to provide compression-resistance to the collagen sponge. The compression-resistant material may comprise ceramic granules. In certain specific embodiments the compression-resistant material comprises biphasic ceramic granules. In some embodiments, the compression-resistant material is biodegradable. In other embodiments, the compression-resistant material is non-biodegradable.

DETAILED DESCRIPTION

Figure 1:
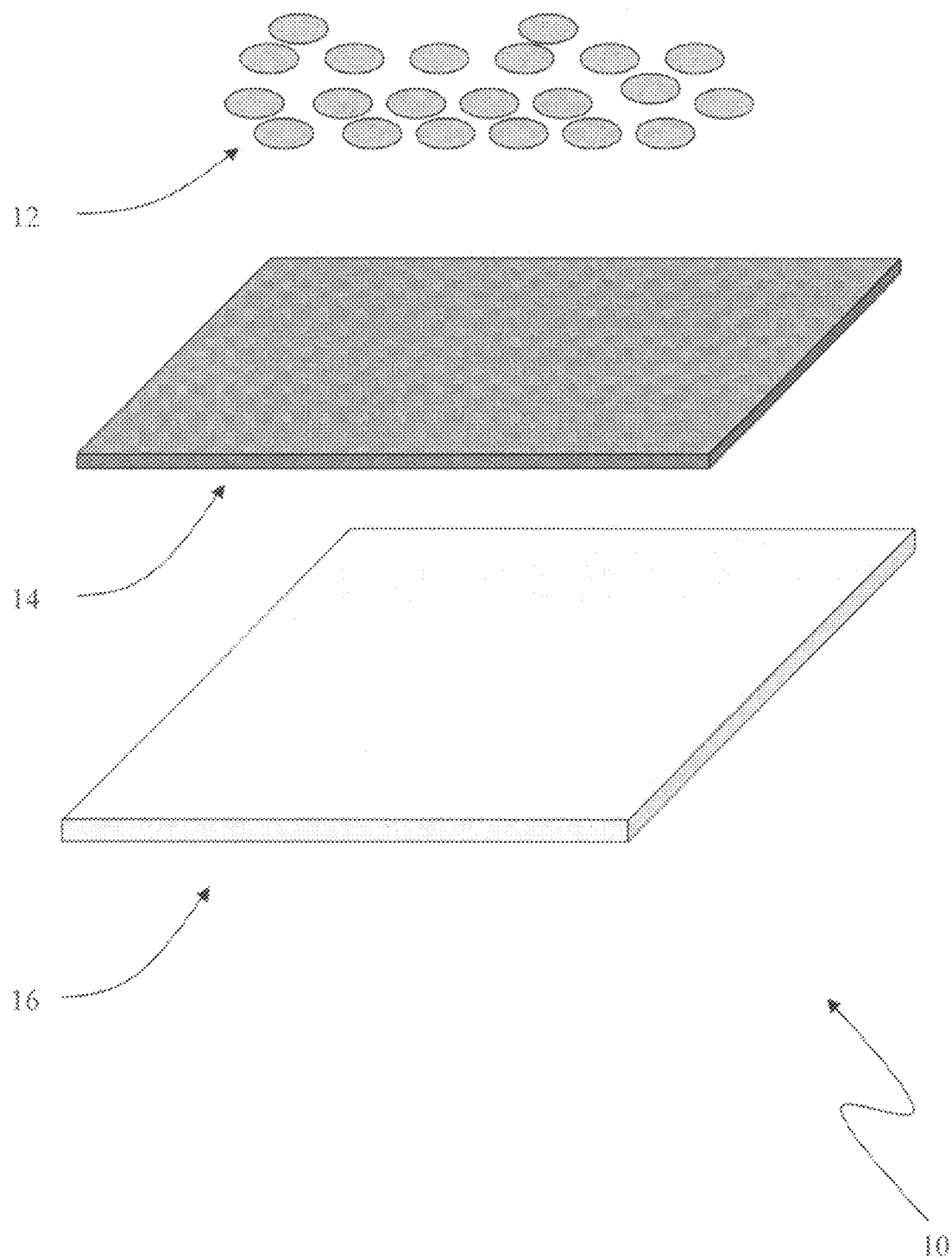
FIG. 1 depicts components of an embodiment rolled carrier.

To better describe the instant invention, the following non-limiting definitions are provided:

The term "osteoconduction" refers to the ability to stimulate the attachment, migration, and distribution of vascular and osteogenic cells within a graft material. The physical characteristics that affect the graft's osteoconductive activity include porosity, pore size, and three-dimensional architecture. In addition, direct biochemical interactions between matrix proteins and cell surface receptors may play a major role in the host's response to the graft material.

The term "osteogenic" refers to the ability of a bone-forming cells to produce new bone independently. To have direct osteogenic activity, a graft material should ideally contain cellular components that directly induce bone formation. For example, a collagen matrix seeded with osteoblasts and/or pre-osteoblasts would have the potential to induce bone formation directly, without recruitment and activation of host cell populations.

The term "osteoinduction" refers to the ability to stimulate the proliferation and differentiation of pluripotent activated mesenchymal stem cells (MSCs) into bone-forming cells, resulting in the induction of new bone. In endochondral bone formation, stem cells differentiate into chondroblasts and chondrocytes, laying down a cartilaginous extracellular matrix (ECM), which subsequently calcifies and is remodeled into lamellar bone. In intramembranous bone formation, the stem cells differentiate directly into osteoblasts, which form bone through direct mechanisms. Osteoinduction can be stimulated by osteogenic growth factors, although some ECM proteins can also drive progenitor cells toward the osteogenic phenotype. Osteoinduction also refers to the ability to attract cells to a site through chemotactic signaling. For example, certain growth factors will attract MSCs to the site prior to proliferation and differentiation.

The term "osteopromotive" refers to factors that facilitate bone formation but are insufficient to drive bone formation like osteoinductive factors.

"Growth factors" includes factors that are osteogenic, osteoinductive, osteopromotive or combinations thereof.

The term "angiogenesis" refers to the stimulation and generation of the growth of new blood vessels, and particularly within an AVN region of bone. Certain growth factors (e.g., VEGF) can directly stimulate this angiogenic effect, while other growth factors (e.g., BMP) indirectly stimulate this effect by causing local cells to release VEGF.

The term "patient" refers to a biological system to which a treatment can be administered. A biological system can include, for example, an individual cell, a set of cells (e.g., a cell culture), an organ, or a tissue. Additionally, the term "patient" can refer to animals, including, without limitation, humans.

The term "treating" or "treatment" of a disease refers to executing a protocol, which may include administering one or more drugs to a patient (human or otherwise) in an effort to alleviate signs or symptoms of the disease. Alleviation can occur prior to signs or symptoms of the disease appearing as well as after their appearance. Thus, "treating" or "treatment" includes "preventing" or "prevention" of disease. In addition, "treating" or "treatment" does not require complete alleviation of signs or symptoms, does not require a cure, and specifically includes protocols which have only a marginal effect on the patient.

The terms "overstuffing" and "overpacking" refer to the insertion of an undesirably high concentration of growth factor into a pre-drilled space in the bone of a patient. Overstuffing or overpacking of BMP on a collagen carrier is associated with bone resorption prior to new bone formation. (See Burkus, et al., "Short-term effects of rhBMP-2/absorbable collagen sponge in a cancellous bone environment," *The Spine Journal* 6:73S-74S (2006).) Bone resorption could result in further collapse of the bone if overstuffing or overpacking occurred during core decompression treatment. Overstuffing may result, for example, when a carrier having a certain concentration of growth factors is placed into a pre-drilled space that is too small for that carrier. This results in a higher concentration of growth factors within the space. For example, overstuffing may result when 6 cc of a carrier material with a starting concentration of 1.5 mg/cc of a growth factor is placed into a 3 cc space, thus resulting in a final concentration of 3.0 mg/cc within the space.

The term "practitioner" refers to a person or persons who practice the methods and systems of the instant invention on the patient. The term includes, without limitations, doctors, nurses, veterinarians and scientists.

An "effective amount" of a bioactive substance, such as a growth factor, is an amount determined by a practitioner to be suitable to provide treatment to a patient. It will be appreciated that this amount may vary depending on the age, sex, health or other factors of the patient, as well as on the type and concentration of bioactive substance administered. The effective amount may exist as a range, with a lower and upper limit. The lower limit may be a level below which no clinically effect is observed. The upper limit may be the level at which complications or undesirable effects exist or the level at which too high of a risk for complications or undesirable effects exist.

To appropriately treat AVN the disorder may first be identified. Identification may be performed by MRI techniques to establish a visual image of the AVN area. MRI is a sensitive and specific technique used for early diagnosis of AVN, and hence the region of interest can be identified and treatment can be started before collapse of the femoral head or other bone structures. Once the region of interest has been identified, if invasive procedures are required, then the standard surgical procedures for gaining access to the target site are used for implantation of the growth factors. If percutaneous procedures are used to implant the growth factors, then appropriate procedures (as described in the following) may be used to deliver the implant to the target sites. That is, the embodiment procedures may be used to administer the therapeutic agent to the target site for the stimulation of angiogenesis, the formation of new bone, or both.

To improve the treatment shortcomings of AVN in the previously described procedures, an angiogenic procedure may be desirable. That is, it may be desirable to perform a procedure that increases the blood supply to the AVN area through the stimulation of blood vessel generation with the use of growth factors implanted to the target site to generate new blood vessel growth, either directly or indirectly as previously described.

For the purposes of promoting an understanding of the principles of the invention, reference to preferred embodiments and specific language will be used to describe the same. It will nevertheless be understood that no limitation of the scope of the invention is thereby intended and that alterations and further modifications of the invention and such further applications of the principles of the invention as herein being contemplated would normally occur to one skilled in the art to which the invention relates.

Bone normally has an internal mesh-like structure, the density of which may vary at different points. However, AVN causes loss of bone tissue, that is, the death of the cellular elements of bone. During this process the outline of individual cells may become indistinct and the affected cells may also merge forming a granular amorphous material. This process also leads to reduced density such that the bone microarchitecture is disrupted and the amount and variety of non-collagenous proteins in the bone is changed. In other words, the porosity of the spacing of the bone tissue in normal bone is much denser than that of the porosity of the spacing of the bone tissue in AVN bone. AVN bone tends to exhibit a decreased number of cells due to cellular necrosis. The amount of bone tissue decreases due to a lack of blood supply. Such a decrease in bone also eventually results in an increase in spacing. The AVN bone then cannot withstand normal stresses associated with body weight or mobility, and fracture or collapse of the bone may thus occur.

In a first aspect, a system is provided for percutaneous delivery of a growth factor to a pre-drilled space in a bone of a patient. The system includes an applicator having a hollow core extending along the length of the applicator, with proximal and distal ends, and with a length such that when the distal end of the applicator is in contact with a pre-drilled space in a bone the proximal end is exposed; a carrier having one or more growth factors, the carrier being of a size capable of being inserted into the pre-drilled space through the core of the applicator; and a pusher device capable of advancing the carrier through the applicator and into the pre-drilled space without overstuffing the carrier.

In one embodiment the carrier includes a collagen sponge material, which may be rolled into a substantially cylindrical shape and may also be wrapped by a flexible, sterile sheet. The carrier may also include a compression resisting material. The compression resisting material is designed to provide the sponge material compression resistance characteristics. The compression resisting material may take any suitable form; for example, the compression resisting material may be a rod around which the sponge material is wrapped. Alternatively, the compression resistance material may take the form of granules, which can collectively impart compression resistance to the sponge material. In a preferred embodiment the carrier includes ceramic granules, preferably biphasic ceramic granules, which may be placed on the collagen sponge material prior to being rolled into a substantially cylindrical shape. In another embodiment the carrier may be formed from a collagen/ceramic matrix material, such as Mastergraft® (Medtronic, Inc., Minneapolis, Minn.). A collagen/ceramic matrix material is typically formed by physically mixing together ceramic granules with collagen; the collagen is then cross-linked, using either chemical or physical processes, resulting in a pre-formed shape that resists compression and which may also serve as a carrier for the growth factor. The compression-resistant material may be biodegradable or non-biodegradable.

In one embodiment the growth factor is in solution, which may be soaked into or applied onto the collagen sponge material. In another embodiment a growth factor solution may be soaked into or applied onto the biphasic ceramic granules. In another embodiment, the growth factor solution may be soaked into or applied onto the collagen/ceramic matrix.

The growth factors include, but are not limited to, bone morphogenetic proteins (BMPs), their recombinant versions and recombinant human versions, such as BMP-2, rhBMP-2, BMP-4, rhBMP-4, BMP-6, rhBMP-6, BMP-7 (also known as OP-1), rhBMP-7, BMP-9, rhBMP-9, fragments derived from the various BMPs, GDF-5, and rhGDF-5, as disclosed, for example, in U.S. Pat. Nos. 4,877,864; 5,013,649; 5,661,007; 5,688,678; 6,177,406; 6,432,919; 6,534,268; and 6,858,431; and in Wozney, J. M., et al. (1988) *Science,* 242(4885):1528-1534. Bone morphogenetic proteins have been shown to be excellent at growing or inducing the growth of new bone, several products are currently undergoing tests. Extensive animal testing has already been undertaken, and human trials are either completed or in process for these products. rhBMP-2 delivered on an absorbable collagen sponge (ACS) (such as INFUSE® Bone Graft, Medtronic Sofamor Danek, Memphis, Tenn.) has been used inside titanium fusion cages and resulted in fusion in 11 out of 11 patients in a pilot study and in 99% of over 250 patients in a pivotal study. On Jul. 2, 2002, INFUSE® Bone Graft in combination with certain metal cages received FDA approval for use in certain types of spine fusion. A pilot study with BMP-2 delivered on a ceramic carrier was recently published and reported a 100% successful posterolateral fusion rate. BMP-7 (OP-1) has reported 50-70% successful posterolateral lumbar fusion results in human studies to date. On Apr. 30, 2004, INFUSE® Bone Graft was approved for acute, open fractures of the tibial shaft (Bosse et al. *NEJM* 347(24): 1924-1931, 2002; Govender et al. *JBJS* 84(12): 2123-2134, 2002). Studies with these and other BMPs are underway. The present invention may apply these growth factors to bone with AVN. These growth factors stimulate the growth of new blood vessels to prevent further AVN and also reverse the AVN process. The treatment of AVN is a novel use of these growth factors for depot implants.

Additionally, suitable growth factors may also include, without limitation, platelet-derived growth factor (PDGF), transforming growth factor β (TGF-β), insulin-related growth factor-I (IGF-I), insulin-related growth factor-II (IGF-II), fibroblast growth factor (FGF), beta-2-microglobulin (BDGF II) (as disclosed in U.S. Pat. No. 6,630,153), PTH, PGE2-agonist, granulocyte colony stimulating factor (G-CSF), vascular endothelial growth factor (VEGF), matrix metalloproteinase (MMP), statins, recombinant versions thereof and recombinant human versions thereof.

Referring now to FIG. 1, the elements of one embodiment of a carrier 10 are shown in exploded view. A compression resisting material, which may, for example, be in the form of biphasic ceramic granules 12, may be rolled up within a collagen sponge material 14. The collagen sponge material 14 may be used as a carrier for an effective amount of a growth factor solution, which may be soaked into or applied onto the sponge 14. While it may be preferable to apply the growth factor to the collagen sponge material prior to adding the compression-resistant material to the collagen sponge material, one may apply the growth factor to the collagen sponge material after adding the compression-resistant material to the collagen sponge material. Alternatively, the growth factor solution may be soaked into the biphasic ceramic granules 12. A flexible, sterile sheet 16 may be used to roll up the collagen sponge material 14 and the biphasic ceramic granules 12.

Figure 2A:
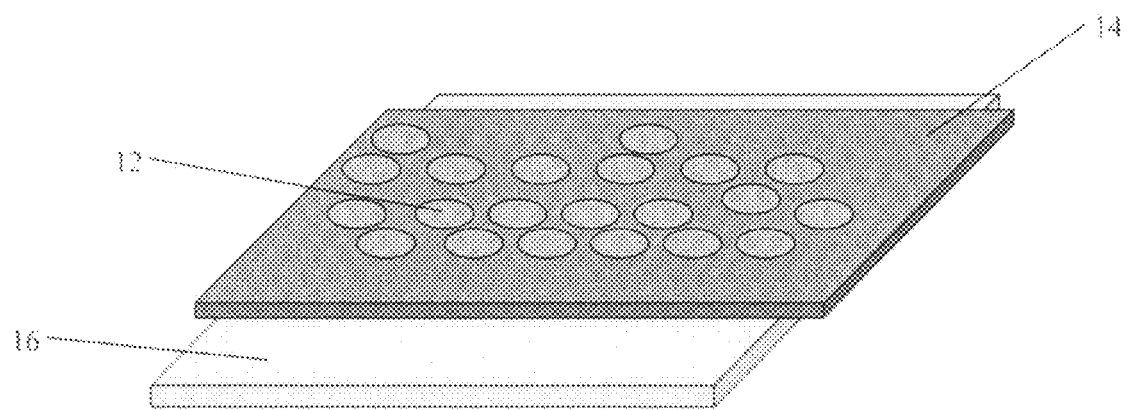
FIGS. 2A and 2B depict stages during the assembly of an embodiment rolled carrier.
Figure 2B:
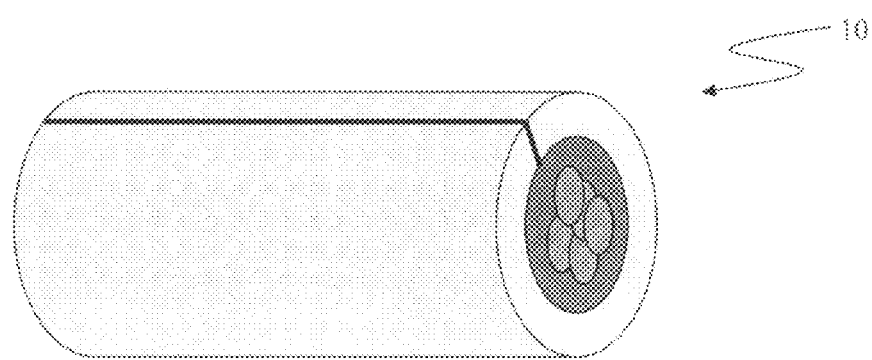

FIGS. 2A and 2B depict the components of FIG. 1 in combination. As shown in FIG. 2A, the compression resisting material, such as biphasic ceramic granules 12, may be placed on or within the collagen sponge material 14, and the combination of these elements may then be placed on top of the flexible, sterile sheet 16. In one embodiment, a growth factor solution, having a therapeutically effective amount of a growth factor, such as rhBMP-2, may be soaked into the collagen sponge material 14. The biphasic ceramic granules 12 may then be placed on the collagen sponge material 14, and the combination placed on the flexible, sterile sheet 16, which, as shown in FIG. 2B, may then be used to roll up the combination to provide the implant 10. The compression resisting material 12 provides the implant 10 with compression resistance properties so that the implant 10 avoids overstuffing when placed into the target space within bone. By resisting compression, the implant 10 ensures that the proper amount of growth factor is disposed within the proper amount of volume; i.e., the concentration of the growth factor within the target site is correct. Additionally, by resisting compression, the implant 10 ensures that the concentration of the growth factor remains relatively uniform all across the implant 10; i.e., the compression-resistant implant 10 avoids local "hot spots" of the growth factor that might otherwise arise from compression of the sponge material 14 that is impregnated with the growth factor. In another embodiment, the growth factor solution may be soaked into the biphasic ceramic granules 12 prior to their placement on the collagen sponge material 14. The combination is then placed on the flexible, sterile sheet 16, which is used to roll up the combination to form the implant 10. These embodiments may be referred to as a "rolled implant" or "fajita-style roll" carrier.

The depictions of FIGS. 2A and 2B represent an embodiment of the fifth aspect of the invention, which provides a carrier 10 for insertion into a pre-drilled space in a bone of a patient. The carrier 10 includes a flexible, sterile sheet 16; a collagen sponge 14 placed on one face of the flexible, sterile sheet 16, the collagen sponge 14 having an effective amount of a growth factor. The flexible, sterile sheet 16 is rolled into a cylindrical shape to form a substantially cylindrically-shaped implant 10, with the flexible, sterile sheet 16 being on the outside of the cylindrical shape. The cylindrical shape is of a length such that it may be inserted into the pre-drilled space without being overstuffed or overpacked. For example, the length and diameter of the implant may be respectively substantially the same as the depth and diameter of the pre-drilled space.

Figure 3:
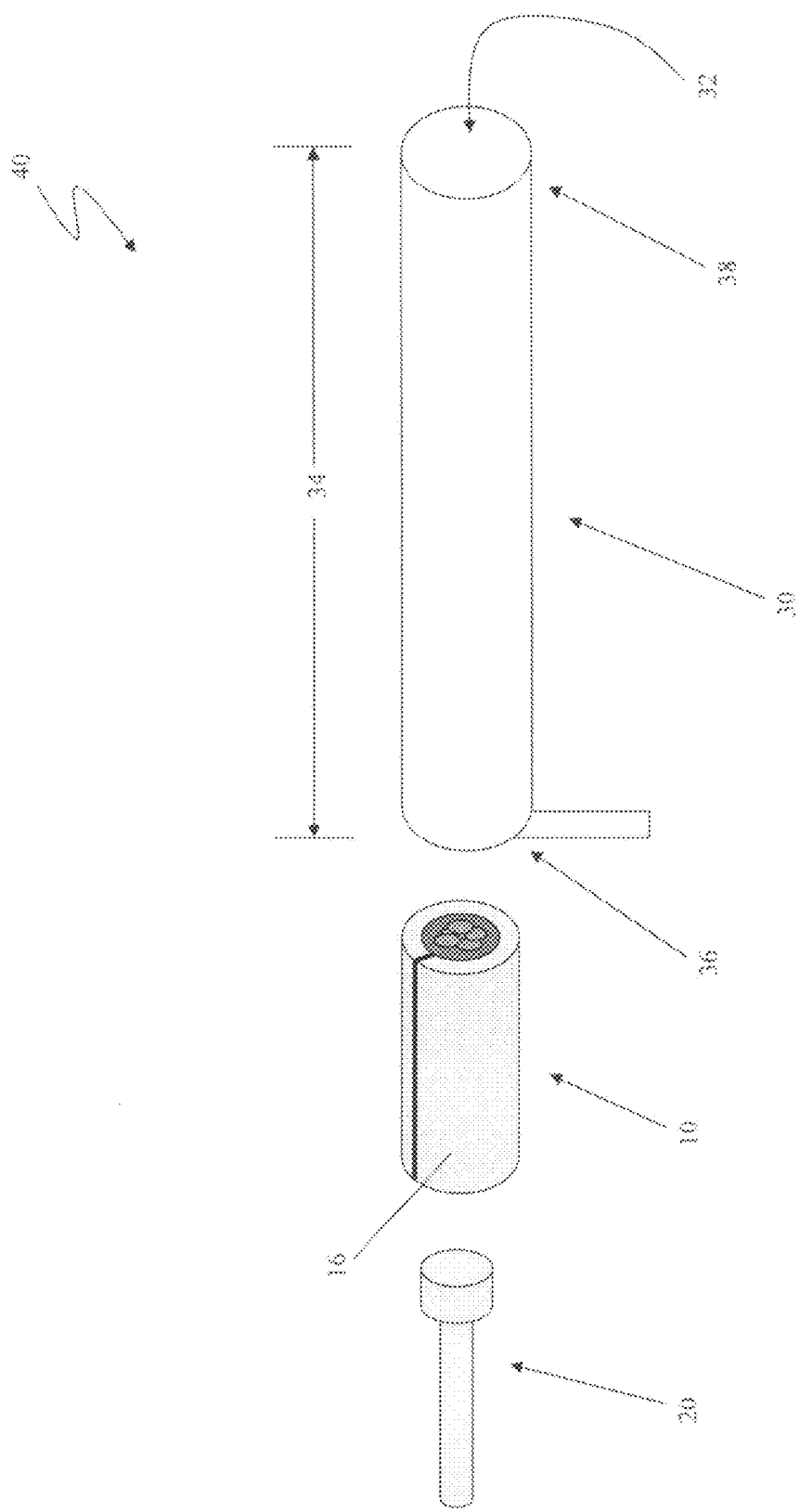
FIG. 3 is an exploded view of a percutaneous applicator, a rolled carrier, and pusher device of one embodiment system.

FIG. 3 depicts elements of one embodiment of a system 40 according to the first aspect of the invention. The system 40 includes a pusher device 20, which may be used to push the carrier 10, for example, distally through an applicator 30 and into a pre-drilled space in a bone of a patient. The rolled carrier 10, as described above, may be pushed through the applicator 30 and inserted into a pre-drilled space in a bone of a patient. The applicator 30 may have a hollow core 32 extending along the length 34 of the applicator 30, and may be of a length such that when a distal end 38 of the applicator is in contact with or inserted into a pre-drilled space in a bone the proximal end 36 is exposed (that is, is not embedded within tissue of the patient), permitting a practitioner to insert the carrier 10 into the applicator 30 and, if necessary, use the pusher device 20 to distally push the carrier 10 into the pre-drilled space. In certain embodiments the applicator 30 may be formed from metal or plastic tubing. The core 32 of the applicator 30 is ideally of a sufficient diameter that the carrier 10 can fit through the applicator 30 and be brought into contact with the bone surface of the patient. In certain specific embodiments the pusher device 20 and applicator 30 are designed to mechanically engage with each other to avoid overstuffing of the carrier 10 into the pre-drilled space. For example, after the pusher device 20 has advanced distally to a position that corresponds to an optimal positioning of the carrier 10 within the pre-drilled space, a notch, tab, break or any others suitable mechanism on the applicator 30 may mechanically engage with the pusher device 20 to prevent further distal advancement of the pusher device 20. Alternatively, the pusher device 20 and applicator 30 may mechanically engage with each other to signal that the optimum distal position has been reached, such as by a change in force needed to continue advancing the pusher device 20, by creating a clicking sound or sensation, or the like. The sterile sheet 16 may provide a relatively smooth surface that eases and facilitates the distal advancement of the implant 10 within the confines of the pre-drilled space, thus reducing the force needed to advance the implant 10, and thus avoid compression of the implant 10. Use of the pusher 20 and the sterile sheet 16 help to minimize the potential for overpacking of the carrier 10. The entire roll (carrier 10 and sterile sheet 16) may be placed within the pre-drilled space. The pusher device 20 would then press against the carrier 10, but allow the sterile sheet 16 to be withdrawn past the pusher and then removed from the patient. In this embodiment, the sterile sheet 16 could be longer than both the carrier 10 and the applicator 30 to facilitate removal of the sterile sheet 16 while the pusher device 20 holds the carrier 10 within the pre-drilled space. The flexible sterile sheet 16 could be made of a material which is stiffer and more tear-resistant than the carrier material. Once the sterile sheet 16 is removed, the carrier 10 would be left in direct contact with the surrounding bone within the pre-drilled space and would be evenly spread across that space without tearing or overstuffing.

Figure 4:
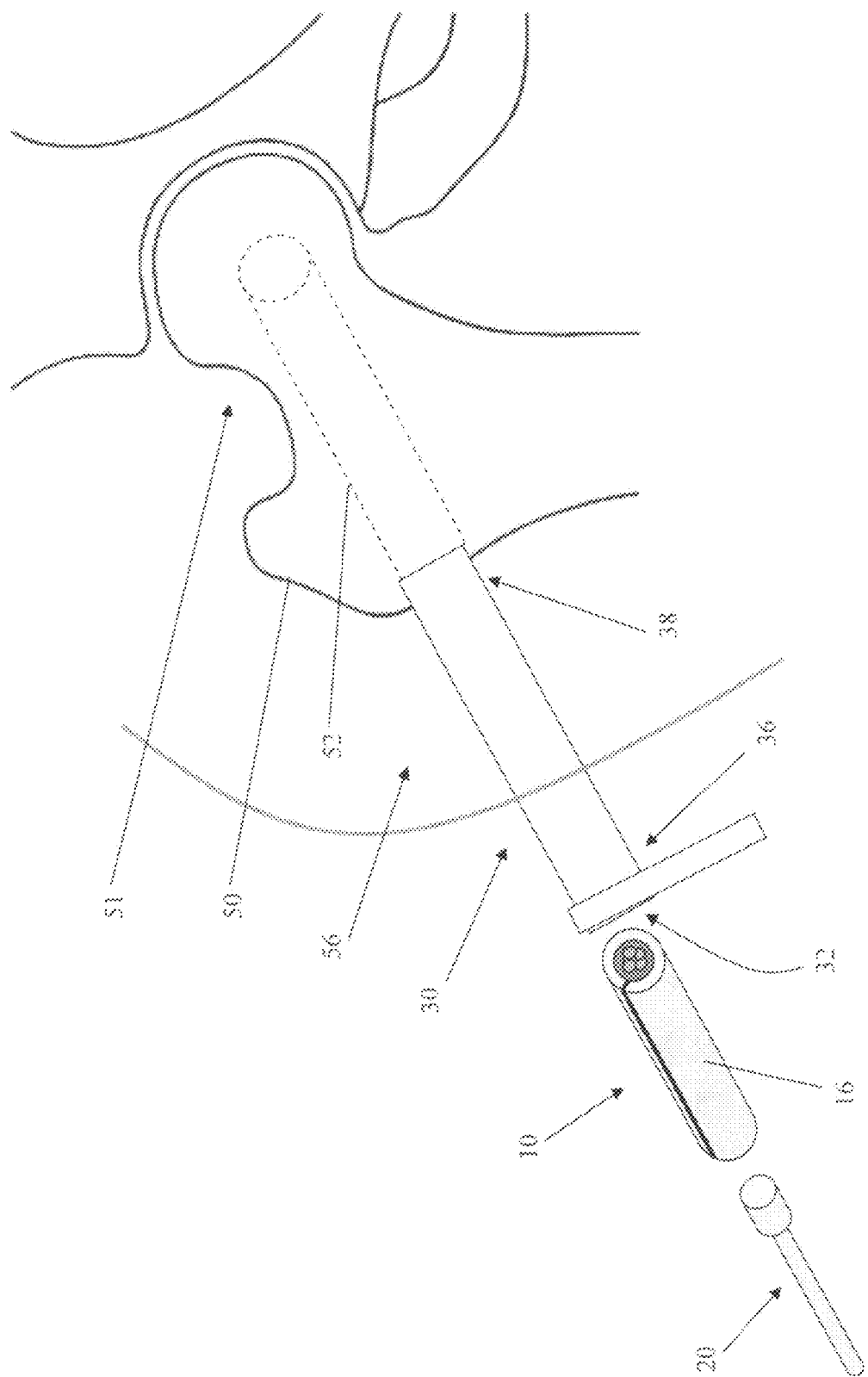
FIG. 4 illustrates a percutaneous applicator, a rolled carrier, and a pusher device of an embodiment system in relation to a pre-drilled space in a patient's femur.

FIG. 4 depicts an embodiment in which the system is used to insert the carrier 10 into a pre-drilled space 52 in the femoral head 51 of a patient. The pre-drilled space 52 is formed as part of a core decompression treatment for AVN of the femoral head 51. The applicator 30 is sufficiently long to allow access to the pre-drilled space 52 through muscle and soft tissue 56. The rolled carrier 10 fits through the core 32 of the percutaneous applicator 30, and the distal end 38 of the applicator 30 may be brought into contact with the bone surface of the femur 50. The carrier 10 may be inserted into the exposed, proximal end 36 of the percutaneous applicator 30 and pushed into the pre-drilled space 52 with use of the pusher device 20. In one embodiment, the flexible sterile sheet 16, pusher device 20, and percutaneous applicator 30 are removed from the patient after insertion of the carrier 10 into the pre-drilled space 52. Forceps, for example, may be used to remove the sterile sheet 16. Alternatively, the sheet 16 may be made longer than the rest of the carrier 10. Once the carrier 10 is in position, the sheet 16 may be pulled proximally back out of the applicator 30 while the pusher device 20 remains in position to keep the remainder of the implant 10 in place within the pre-drilled space 52. FIG. 4 thus illustrates an embodiment method of delivering an effective amount of one or more growth factors to the pre-drilled space 52 within the bone 50 of a patient in a manner that prevents overstuffing of the carrier 10.

Figure 5:
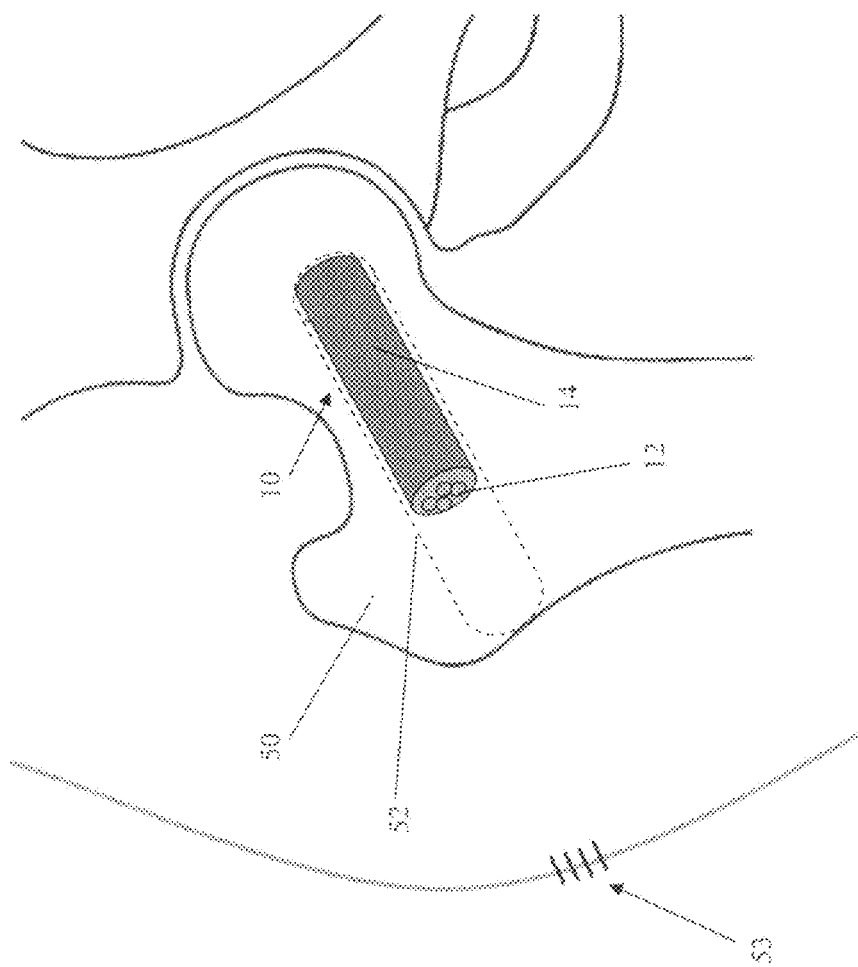
FIG. 5 illustrates a percutaneous applicator, a sterile sheet, a pusher device, and a carrier after removal of the percutaneous applicator, sterile sheet, and pusher device from the patient.
Figure 5:
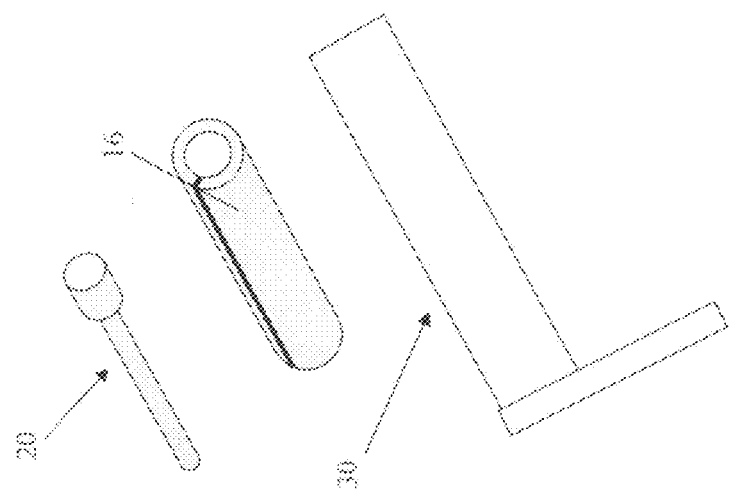

FIG. 5 depicts the system 40 after performing an implant insertion procedure. In one embodiment, after insertion of the carrier 10 into the pre-drilled space 52, the flexible, sterile sheet 16, pusher device 20, and percutaneous applicator 30 are removed from the patient; the remainder of the carrier 10, including collagen sponge material 14, compression-resistant material, such as biphasic ceramic granules 12, and an effective amount of one or more growth factors, is left within the bone 50 of the patient. The growth factors may be disposed within the collagen sponge material 14, the compression resistant material 12, or both. In another embodiment, the carrier 10 may not include the compression resisting material 12. Once the applicator 30 and sheet 16 have been removed from the patient, the incision 53, through which the applicator 30 was passed to gain access to the pre-drilled hole 52, may be sutured.

Figure 6:
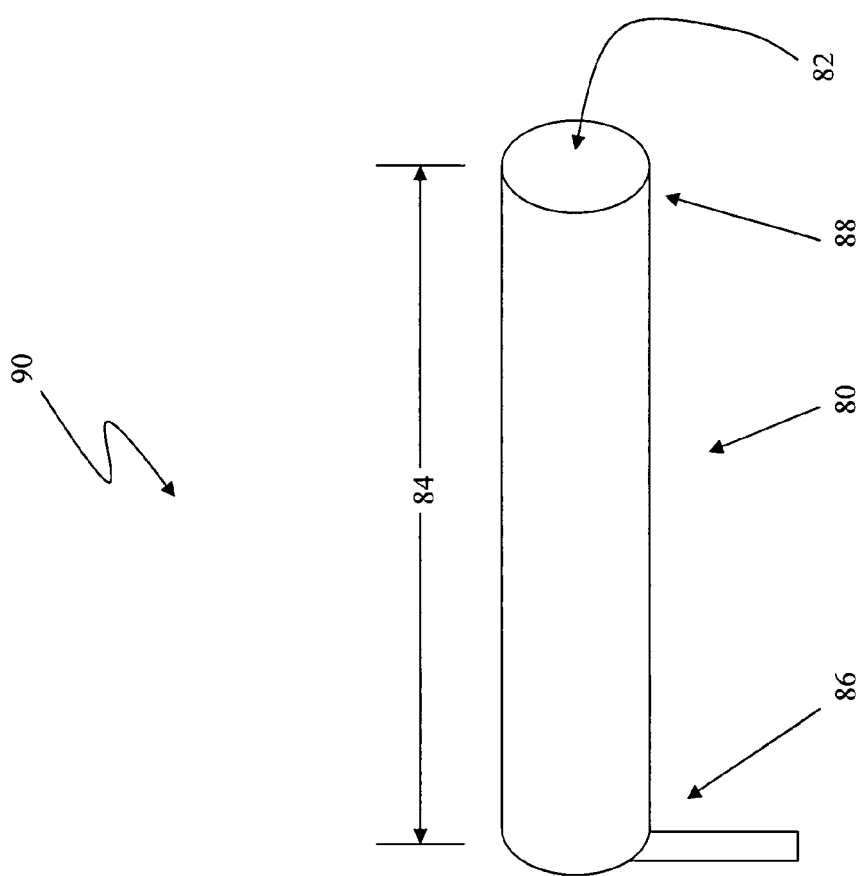
FIG. 6 is an exploded view of a percutaneous applicator, a biphasic matrix carrier, and a pusher device of another embodiment system.
Figure 6:
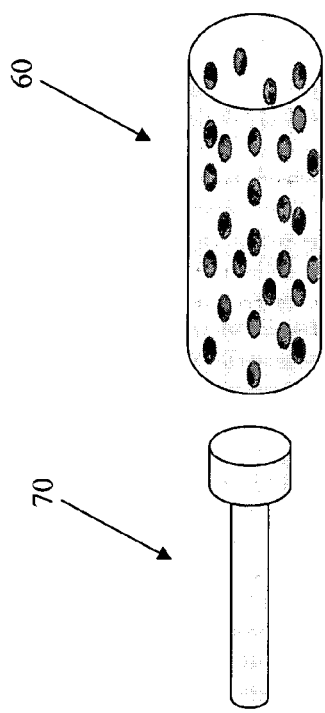

FIG. 6 depicts elements of another embodiment system 90. A pusher device 70 may be used to push a carrier 60 through an applicator 80 and into a pre-drilled space in a bone of a patient. In one embodiment, the carrier 60 may be the collagen sponge material containing one or more growth factors, the collagen sponge material being wrapped around compression-resistant material, such as biphasic matrix granules, and may be pushed through the applicator 80 for insertion into a pre-drilled space in the bone of the patient. In another embodiment, the carrier 60 may be formed from a mixture of ceramic granules, preferably biphasic ceramic granules, and collagen, in which the collagen has been cross-linked to provide a pre-shaped form. The carrier will have compression resisting properties. The growth factor may be added to the entire carrier 60. The percutaneous applicator 80 may have a hollow core 82 extending along the length 84 of the applicator 80 and may be of a length such that when one end 88 of the applicator 80 is in contact with or inserted into a pre-drilled space in the bone the other end 86 is exposed, permitting a practitioner to insert the carrier 60 into the applicator 80 and, if necessary, push the carrier 60 through the hollow core 82 into the pre-drilled space. In certain embodiments the applicator 80 may be made from metal, plastic tubing, or any other suitable material. The core 82 of the applicator 80 is of a sufficient diameter such that the carrier 60 can slide through the applicator 80 and be brought into contact with the bone of the patient. The pusher 70 may be designed to mechanically engage with the applicator 80 once a predetermined distal advancement of the pusher 70 has been reached, as previously described. Use of the pusher 70 may thus further minimize potential for overstuffing or overpacking of the carrier 60.

Figure 7:
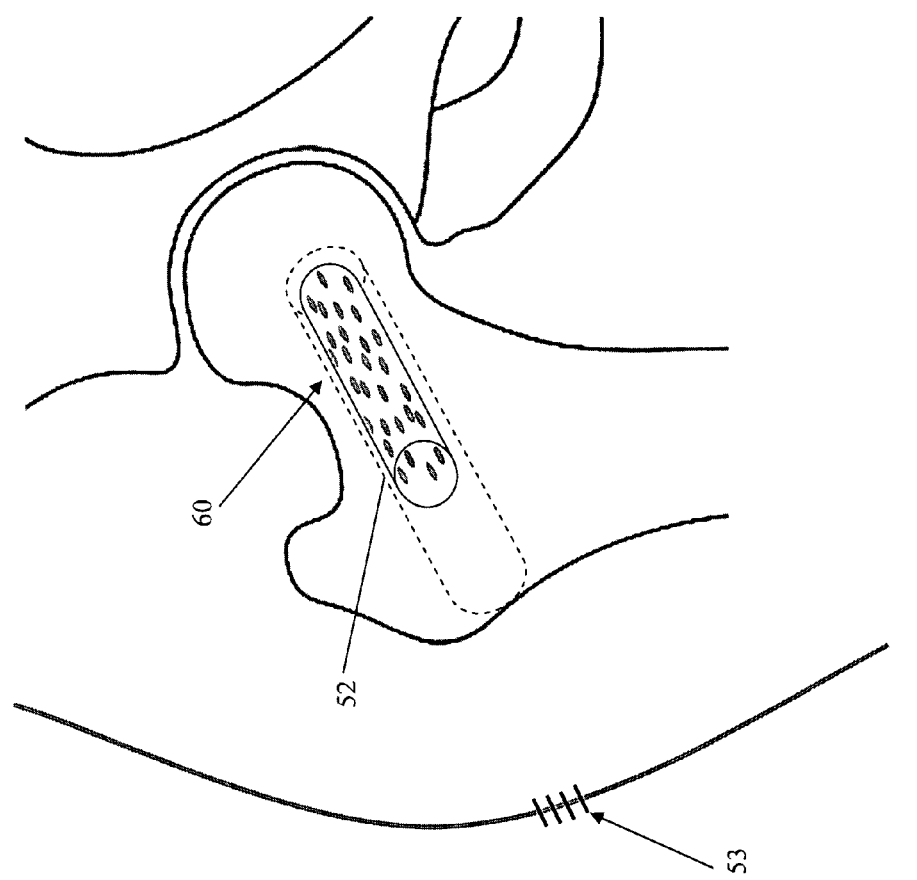
FIG. 7 shows a percutaneous applicator, a pusher device, and a biphasic matrix carrier after removal of the percutaneous applicator and pusher device from the patient.
Figure 7:
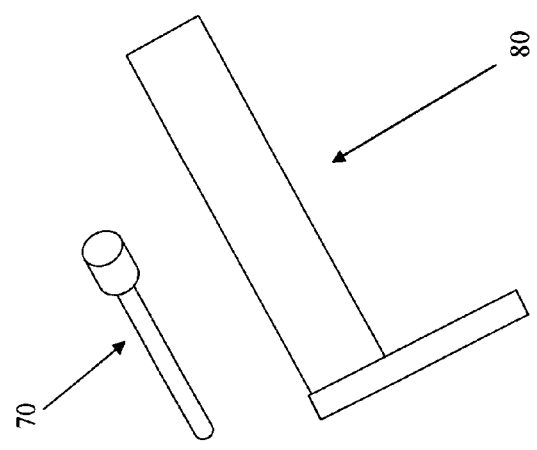

FIG. 7 depicts the system 90 and the patient after implantation of the carrier 60. After insertion of the carrier 60 into the pre-drilled space 52, the pusher device 70 and percutaneous applicator 80 are removed from the patient; the biphasic matrix carrier 60, which has an effective amount of a growth factor, is left within the patient. The incision 53 may then be sutured.

Figure 8:
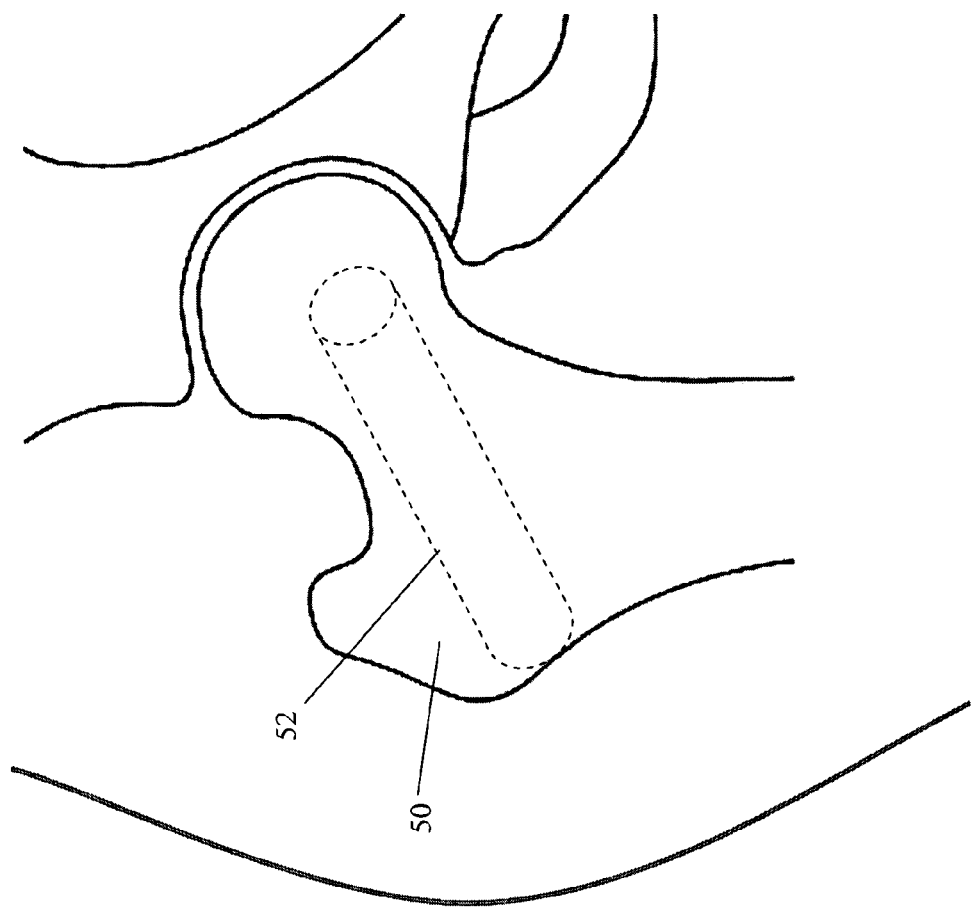
FIG. 8 shows a threaded applicator and a carrier of yet another embodiment system in relation to a pre-drilled space in a patient's femur.
Figure 8:
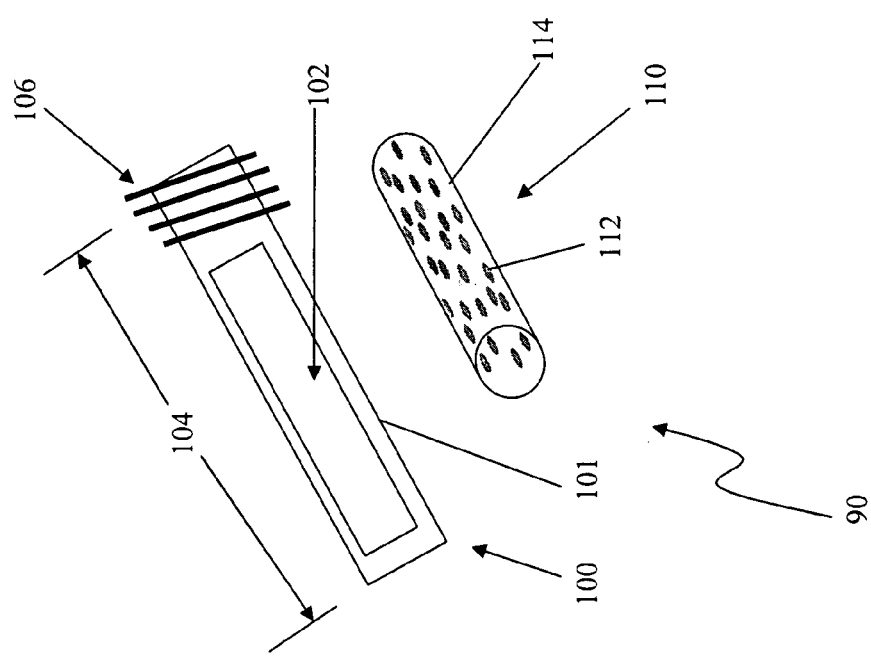

FIG. 8 depicts another embodiment system 90. The system 90 includes a threaded applicator 100 and a carrier 110. The threaded applicator 100 has a hollow core 102. The threaded applicator may have spaces, slots, or holes along its side and/or its bottom which allow for substances to exit and enter the interior of the threaded applicator. The length 104 of the threaded applicator 100 is such that the threaded applicator 100 will fit into the pre-drilled space 52 in the bone 50 of a patient. The threaded applicator 100 also includes threads 106 along at least a portion of the outside surface 101 of the threaded applicator 100, which are designed to enable the threaded applicator 100 to mechanically engage with the bone 50 of the pre-drilled hole 52. The threads may be continuous, so that the threaded applicator may be screwed into the pre-drilled hole 52. Alternatively, the threads may be discontinuous, but angled or otherwise formed so that the threaded applicator 100 may be relatively easily advanced into the pre-drilled hole 52, but will resist backing out of the pre-drilled hole 52. The carrier 110 includes an effective amount of one or more growth factors and may be inserted into the core 102 of the threaded applicator 100 without overstuffing the carrier 110. That is, the size of the carrier 110 is designed to fill the volume within the threaded applicator 100 without overstuffing, so as to provide the correct amount of growth factor to a predetermined volume as defined by the threaded applicator 100. In addition, the carrier 110 may be compression resistant by any of the techniques described herein. In certain embodiments, the threaded applicator 100 is biocompatible and may be left within the patient. The threaded applicator 100 may be formed from plastic, metal, ceramic or any other suitable material. The threaded applicator 100 physically prevents the overstuffing of the carrier 110 when placed within the pre-drilled space 52. Additionally, the threaded applicator 100 may provide physical support for the patient when disposed within the space 52.

Any of the previously disclosed carriers may be inserted into the core 102 of the threaded applicator 100 to serve as the carrier 110. For example, in certain embodiments, the carrier 110 may be the carrier 60 discussed in reference to FIG. 6. In other embodiments, the carrier 10 discussed in reference to FIGS. 2A and 2B may be used as the carrier 110 within the threaded applicator 100. In yet another embodiment, the carrier 110 may be similar to the rolled carrier 10, but without the sterile sheet 16.

In one embodiment the growth factor is in solution, which may be soaked into or applied onto the collagen sponge material 114. In another embodiment the growth factor solution may be soaked into the biphasic ceramic granules 112 or other compression-resistant material.

In different, non-limiting embodiments of the invention, the growth factor of the invention may be a bone morphogenetic protein, or fragments thereof, such as BMP-2, rhBMP-2, BMP-4, rhBMP-4, BMP-6, rhBMP-6, BMP-7 (OP-1), rhBMP-7, BMP-9, rhBMP-9, GDF-5, or rhGDF-5, or the growth factor may be selected from the group consisting of platelet-derived growth factor (PDGF), transforming growth factor β (TGF-β), insulin-related growth factor-I (IGF-I), insulin-related growth factor-II (IGF-II), fibroblast growth factor (FGF), beta-2-microglobulin (BDGF II) (as disclosed in U.S. Pat. No. 6,630,153), PTH, PGE2-agonist, granulocyte colony stimulating factor (G-CSF), vascular endothelial growth factor (VEGF), matrix metalloproteinase (MMP), and statins. Recombinant, and recombinant human versions of the growth factors may also be used, such as rhPDGF, rhTGF-β, etc.

Figure 9:
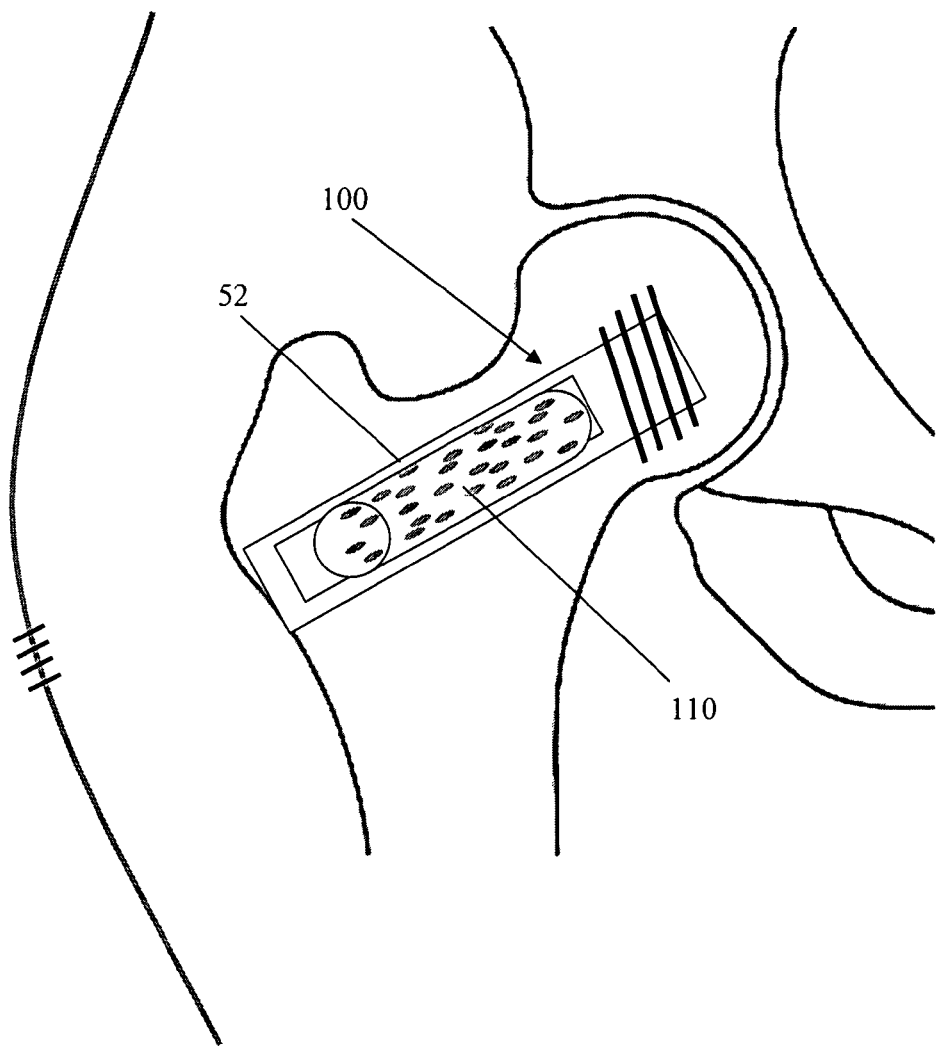
FIG. 9 illustrates a threaded applicator and a carrier after insertion into the pre-drilled space in a patient's femur.

As shown in FIG. 9, after insertion of the threaded applicator 100 into the pre-drilled space 52, the threaded applicator 100 and matrix carrier 110 having an effective amount of one or more growth factors may be left within the patient. The matrix carrier 110 may be inserted into the threaded applicator 100 before or after the threaded applicator 100 is placed inside the pre-drilled space 52.

Specific embodiments methods will now be described in the following examples. The examples are illustrative only, and are not intended to limit the remainder of the disclosure in any way.

Example 1

Short-Term Effects of rhBMP/Absorbable Collagen Sponge (ACS) in a Cancellous Bone Environment Bilateral cancellous bone defects (8.0 mm diameter×20.0 mm depth, 1 $cm^3$ volume) in distal femurs of 30 adult sheep are created. To study the effect of increasing the overall rhBMP-2 dose or concentration in cancellous bone, rhBMP-2/ACS implant volume (V) (1V=normal or 2V=overfilled) and concentration (1×=normal or 3.5×=hyperconcentrated) are varied. Control defects are treated with buffer/ACS. Animals are killed at 1, 4, and 8 weeks (4 defects per treatment per time point), and the effects on the specimens are assessed using CT scans and histology.

At 1 week, the normal-filled, normal-concentration implants demonstrate limited peri-implant osteoclastic activity. Conversely, overfilled or hyperconcentrated rhBMP-2/ACS implants demonstrate moderate resorption zones with enhanced osteoclastic activity. Implants that are both overfilled and hyperconcentrated demonstrate the most extensive peri-implant resorption with marked osteoclastic activity. In the moderate and marked resorptive zones, free-floating osteoclasts are present suggesting rapid resorption of the peri-implant cancellous bone. However, re-ossification of all peri-implant voids is progressively observed on CT through 8 weeks. Histology at 4 and 8 weeks reveals partially mineralized osteoid in the voids, which continue to heal over time. Defects filled with buffer/ACS do not demonstrate resorption or ossification at any time point.

The cancellous bone environment allows for increased access to host bone cells (i.e., mesenchymal stem cells, osteoblasts, osteoclasts) and provides a worst-case scenario for studying local osteoclastic response to BMP-2 implants. Increasing the total rhBMP-2 dose either by overfilling the defect or by hyperconcentrating rhBMP-2 on the ACS carrier leads to a dose-dependent local osteoclastic resorption of adjacent cancellous bone. However, this effect is transient and progressive healing occurred over the 8-week survival period. This study demonstrates the importance of avoiding overpacking of the ACS carrier within a construct or bony defect.

Example 2

An experiment to study the effect of the addition of a biphasic ceramic bulking agent to the rhBMP-2/ACS implant is completed. Four cancellous bone defects (8.0 mm diameter×20.0 mm depth, 1 $cm^3$ volume) are created in distal femurs of adult sheep. Equal volumes of the rhBMP-2/ACS implant and biphasic ceramic granules are mixed together and place into the cancellous defect. The addition of the ceramic granules physically prevents overstuffing of the defect with the mixture, such that only 1V could be added to each defect. The rhBMP-2/ACS implant is prepared with 4 times the effective concentration (4×), such that the final local concentration within the defect is similar to overfilled defect in the previous experiment (2V at 1×). The effect on the specimens is assessed using CT scans and histology. At 1 week, despite having a local concentration equivalent to the overfilled group tested in the previous example, resorption zones with enhanced osteoclastic activity are not observed in the test specimens. The addition of the ceramic granules prevents overstuffing of the defect and seems to eliminate the osteoclastic resorption response in the surrounding cancellous bone, even with a hyperconcentrated sample. Not wishing to be bound to any one theory, it is possible that the osteoclasts are too busy resorbing the calcium phosphate in the ceramic granules, instead of the cancellous bone. Regardless of the theory, this experiment shows the potential benefit of the proposed invention.

The cancellous bone defects in the distal femurs of adult sheep are an effective animal model for osteonecrosis of the hip in humans.

Every patent and non-patent publication cited in the instant disclosure is incorporated into the disclosure by reference to the same effect as if every publication is individually incorporated by reference.

Although the invention herein has been described with reference to particular embodiments, it is to be understood that these embodiments are merely illustrative of the principles and applications of the present invention. For example, although shown as a single, monolithic piece, it should be understood that the hollow core of the applicator may be formed from one or more tubes or cannulas that may be linked together to provide exposed access to the pre-drilled space within the bone of the patient. It is therefore to be understood that numerous modifications may be made to the illustrative embodiments and that other arrangements may be devised without departing from the spirit and scope of the present invention as defined by the following claims.

What is claimed is:

1. A system for percutaneous delivery of a growth factor to a pre-drilled space in a bone of a patient comprising:
   (a) a threaded applicator having discontinuous threading, the threaded applicator comprising a hollow core having a total volume, and openings wherein the openings are located on the side or bottom of threaded applicator, and the threaded applicator fits into a pre-drilled space in a bone of a patient and mechanically engages with the bone;
   (b) a carrier comprising an effective amount of a growth factor uniformly distributed throughout the carrier, the carrier having a volume less than the total volume of the core to prevent overcrowding of the carrier in the core and the carrier is inserted into the hollow core of the threaded applicator without overstuffing of the carrier or growth factor, the carrier comprising a collagen sponge material and a compression resisting material, wherein the carrier is wrapped by a flexible sterile sheet being a size longer than the carrier, the flexible sterile sheet having a smooth surface and being more tear-resistant than the carrier, the compression resisting material and the flexible sterile sheet preventing compression of the carrier and maintaining uniform distribution of the growth factor throughout the carrier.

2. The system of claim 1 wherein the threaded applicator is adapted to remain within the patient.

3. The system of claim 1 wherein the collagen sponge material is substantially cylindrical.

4. The system of claim 1 wherein the growth factor is a bone morphogenic protein.

5. The system of claim 4 wherein the bone morphogenic protein is selected from the group consisting of BMP-2, rhBMP-2, BMP-4, rhBMP-4, BMP-6, rhBMP-6, BMP-7 [OP-1], rhBMP-7, GDF-5, and rhGDF-5, BMP-9, rhBMP-9, and fragments thereof.

6. The system of claim 1 wherein the growth factor is selected from the group consisting of PDGF, TGF-β, IGF-I, IGF-II, FGF, BDGF II, PTH, PGE2-agonist, G-CSF, VEGF, MMP, statins.

7. The system of claim 1 wherein the flexible sterile sheet is longer than the hollow core.

* * * * *

UNITED STATES PATENT AND TRADEMARK OFFICE
CERTIFICATE OF CORRECTION

| | | |
|---|---|---|
| PATENT NO. | : 8,092,452 B2 | Page 1 of 1 |
| APPLICATION NO. | : 11/751321 | |
| DATED | : January 10, 2012 | |
| INVENTOR(S) | : Stamps et al. | |

It is certified that error appears in the above-identified patent and that said Letters Patent is hereby corrected as shown below:

In Column 3, Line 11, delete "flexible sheet" and insert -- flexible sterile sheet --, therefor.

In Column 3, Line 13, delete "flexible sheet" and insert -- flexible sterile sheet --, therefor.

Signed and Sealed this
Tenth Day of April, 2012

David J. Kappos
*Director of the United States Patent and Trademark Office*